United States Patent
Suydam et al.

(10) Patent No.: US 10,299,702 B2
(45) Date of Patent: May 28, 2019

(54) DEVICES AND METHODS FOR DETERMINING STEP CHARACTERISTICS

(71) Applicant: Zwift, Inc., Long Beach, CA (US)

(72) Inventors: Stephen Suydam, Chicago, IL (US); Meir Machlin, Tel-Aviv (IL); Jason Kaplan, Clarksville, MD (US)

(73) Assignee: Zwift, Inc., Long Beach, CA (US)

( * ) Notice: Subject to any disclaimer, the term of this patent is extended or adjusted under 35 U.S.C. 154(b) by 421 days.

(21) Appl. No.: 14/938,730

(22) Filed: Nov. 11, 2015

(65) Prior Publication Data

US 2017/0127978 A1    May 11, 2017

(51) Int. Cl.
*A61B 5/103* (2006.01)
*A61B 5/00* (2006.01)
*G01P 13/04* (2006.01)

(52) U.S. Cl.
CPC .......... *A61B 5/1038* (2013.01); *A61B 5/7282* (2013.01); *A61B 2562/0219* (2013.01); *G01P 13/04* (2013.01)

(58) Field of Classification Search
None
See application file for complete search history.

(56) References Cited

U.S. PATENT DOCUMENTS

| | | | |
|---|---|---|---|
| 5,807,869 A | 9/1998 | Furuya et al. | |
| 6,493,652 B1 | 12/2002 | Ohlenbusch et al. | |
| 6,513,381 B2 | 2/2003 | Fyfe et al. | |
| 7,912,672 B2 | 3/2011 | Feichtinger et al. | |
| 8,587,515 B2 | 11/2013 | Mucignat et al. | |
| 9,542,706 B2 | 1/2017 | Case, Jr. | |
| 2006/0052983 A1* | 3/2006 | Vock | A43B 3/0005 702/178 |
| 2006/0143645 A1* | 6/2006 | Vock | A43B 3/00 725/9 |
| 2012/0101411 A1 | 4/2012 | Hausdorff et al. | |
| 2012/0259255 A1 | 10/2012 | Tomlinson et al. | |
| 2014/0136324 A1 | 5/2014 | Machlin et al. | |
| 2015/0081245 A1* | 3/2015 | Nagasaka | G01P 3/64 702/141 |

(Continued)

OTHER PUBLICATIONS

Brach et al., Too much or too little step width variability is associated with a fall history in older persons who walk at or near normal gait speed, Journal of NeuroEngineering and Rehabilitation 2005, 2:21, Jul. 26, 2005.

(Continued)

*Primary Examiner* — Tung S Lau
(74) *Attorney, Agent, or Firm* — SoCal IP Law Group LLP; Jonathan Pearce

(57) ABSTRACT

Devices and methods for determining various occurrences and anomalies within a step are provided. A device to determine characteristics of a step includes at least one sensor to measure acceleration of a foot in at least two directions, at least one processor to execute instructions stored in a memory and to determine accelerations in first and/or second directions meet criteria to determine a footstrike and a push off of a foot from a surface. Slipping of feet while walking and running, clipping of feet while walking and running, and tripping and falling while walking and running may be indicators of overall health and fitness, particularly in older individuals.

9 Claims, 11 Drawing Sheets

(56) References Cited

U.S. PATENT DOCUMENTS

2015/0153374 A1* 6/2015 Balakrishnan .......... G01P 13/00
 702/178

OTHER PUBLICATIONS

Hausdorff et al., Increased Gait Unsteadiness in Community-Dwelling Elderly Fallers, Arch Phys Med Rehabil vol. 78. 278-283, Mar. 1997.
Hausdorff et al., Gait Variability and Fall Risk in Community-Living Older Adults: A 1-Year Prospective Study, Arch Phys Med Rehabil vol. 82, 1050-1056, Aug. 2001.
Maki, Gait Changes in Older Adults: Predictors of Falls or Indicators of Fear? Journal of the American Geriatrics Society, vol. 45, No. 3, 313-320, Mar. 1997.
International Search Report and Written Opinion issued in the corresponding application PCT/US2016/061299 dated Feb. 27, 2017.

* cited by examiner

DEVICES AND METHODS FOR DETERMINING STEP CHARACTERISTICS

BACKGROUND

1. Field

The present disclosure relates to devices and methods for analyzing a step, and, more particularly, to devices and methods drawn to determining various occurrences within a step.

2. Discussion of the Background

Anomalies in steps while walking or running appear in various instances and may be used to document or predict health or likelihood of injury. For example, anomalies may include increased stride time variability, increased stride length variability, and increased walking speed variability, which each indicate an increased likelihood of falling. Falling, particularly among older adults, causes substantial injuries, decreases life expectancy, and causes substantial direct medical costs. As such, there is a need for further investigation into the relationship between gait, health, and likelihood of injury from falling.

SUMMARY

Exemplary embodiments of the present invention provide devices and methods for determining various occurrences and anomalies within a step to determine health, gait, and likelihood of injury.

Additional features of the invention will be set forth in the description which follows, and in part will be apparent from the description, or may be learned by practice of the invention.

Exemplary embodiments of the present invention provide a device to determine characteristics of a step, the device including: at least one sensor to measure acceleration of a foot in at least two directions; at least one processor to execute instructions stored in a memory and to control acceleration data measured by the at least one sensor to be stored in the memory, wherein, if the processor determines that acceleration in a first direction is greater than a first direction threshold for a time longer than a first threshold time, and, if the processor determines that acceleration in a second direction meets at least one condition for determination of an event associated with the second direction, the processor determines that the foot impacts a surface.

Exemplary embodiments of the present invention provide a method for determining characteristics of a step, the method including: measuring acceleration of a foot in at least two directions by a device comprising at least one sensor; storing measured acceleration data in a memory of the device; determining whether acceleration in a first direction is greater than a first direction threshold for a time longer than a first threshold time; determining whether acceleration in a second direction meets at least one condition for determination of an event associated with the second direction; and if the acceleration in the first direction is greater than the first threshold for a time longer than the first threshold time and the acceleration in the second direction meets the at least one condition for determination of the event associated with the second direction, the processor determines that the foot impacts a surface.

It is to be understood that both the foregoing general description and the following detailed description are exemplary and explanatory and are intended to provide further explanation of the invention as claimed. Other features and aspects will be apparent from the following detailed description, the drawings, and the claims.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION

Figure 1:
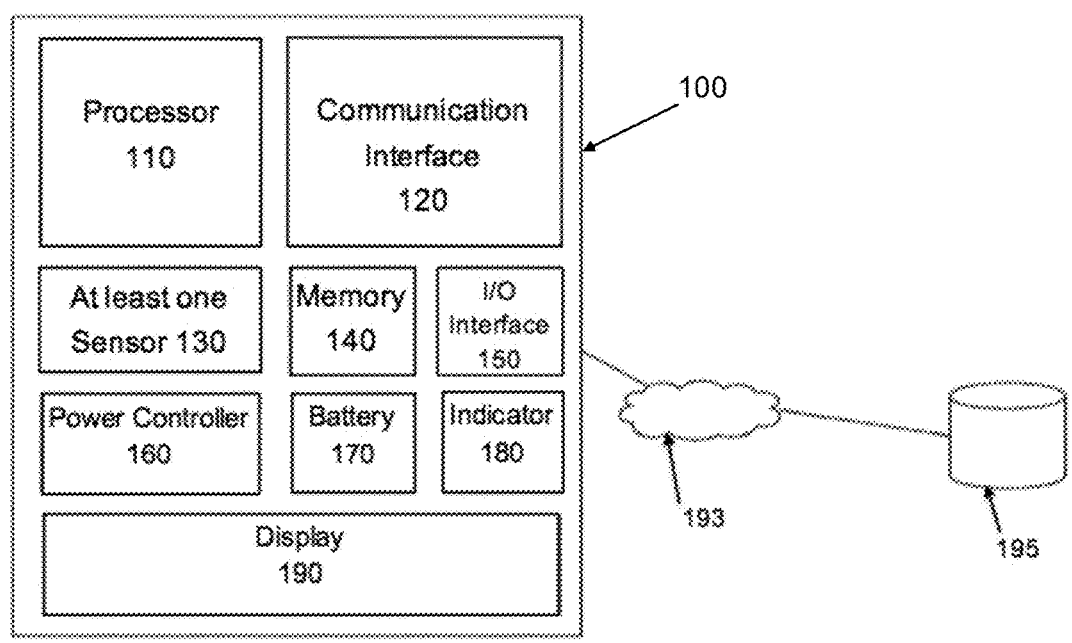
FIG. 1 is a block diagram of a device to measure a step of a walker or a runner according to aspects of the presently disclosed subject matter.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the drawings, like reference numerals denote like elements. The shape, size and regions, and the like, of the drawing may be exaggerated for clarity.

The terminology used herein is for the purpose of describing particular embodiments only and is not intended to be limiting of this disclosure. As used herein, the singular forms "a," "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first," "second," and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In addition to anomalies in steps while walking or running, occurrences and characteristics of the steps of the walker or runner may indicate health and likelihood of injury. For example, a foot may lose traction upon impact with a surface and slip across the surface. Further, a swinging foot, swinging past a stationary foot mid-stride, may strike the stationary foot, which may be referred to herein as clipping the stationary foot. And, a walker or runner may stumble or trip without falling. Slipping of feet while walking and running, clipping of feet while walking and running, and tripping and falling while walking and running may be indicators of overall health and fitness, particularly in older individuals. The importance of determining footstrikes and/or pushoffs accurately increases with age of the individual. Further, monitoring of occurrences, for example, footstrikes and push offs, may indicate fatigue, fitness, health, and injury potential.

FIG. 1 is a block diagram of a device to measure a step of a walker or a runner according to aspects of the presently disclosed subject matter. The device 100 includes a processor 110, a communication interface 120, at least one sensor 130, a memory 140, an input/output (I/O) interface 150, a power controller 160, a battery 170, an indicator 180, and a display 190. Although illustrated and described herein as containing each of the processor 110, the communication interface 120, the at least one sensor 130, the memory 140, the input/output (I/O) interface 150, the power controller 160, the battery 170, the indicator 180, and the display 190, aspects need not be limited thereto such that one or more of the features may be eliminated or combined with other features.

The device 100 is disposed on a walker or runner to capture multiple data readings and measure various aspects of the use of the device 100 using the at least one sensor 130. For example, the device 100 may be attached to the laces of a shoe to directly measure movement of and forces on a foot disposed in the shoe. Aspects need not be limited thereto such that the device 100 may be attached to other portions of a shoe or other clothing as well as at various locations of a user's body; for example, the device 100 may be disposed at a user's wrist, forearm, shoulder, hip, knee, etc. Further, multiple devices 100 may be used to measure different portions of a body. For example, a device 100 may be disposed to monitor a left foot while a second device 100 is disposed to monitor a right foot.

The communication interface 120 assists in and/or controls communication between the device 100 to an external host and/or device 195 to which the device 100 is connectable. The communication interface 120 may support at least one of wired and wireless connections to an external host or device 195, which may be a smartphone, a tablet computer, a laptop computer, a desktop computer, another device 100 or other wearable device, a server, etc. The communication interface 120 of the device 100 may be a serial bus or other hardwire connection. The communication interface 120 of the device 100 may connect the device to such external host or device 195 via a communication connection 193, e.g., cellular and/or data network, a local area network, the internet, and the like. The I/O interface 150 may assist in the communication between the device 100 and the external host or device 195. For example, the I/O interface 150 may be a button or touch sensor, which, when pressed or touched, requests that data stored in the memory 140 be communicated to the external host and/or device 195 via the communication connection 193. The I/O interface 150 may be or further include circuitry or a processor to automatically push or transmit data stored in the memory 140 upon the occurrence of some threshold or event, e.g., detection of a fall, detection of a wireless network, and the like. Further, the I/O interface 150 may operate to reset operability of the device 100 and/or clear the memory 140 according to various presses and/or touches.

The at least one sensor 130 of the device 100 may be one or more of an accelerometer, a magnetometer, a gyroscope, a piezoelectric sensor, a microelectromechanical system (MEMS), a thermometer, a barometer, a moisture sensor, etc., to capture information and or some form of movement or angle of operations of the device 100 disposed on a walker or runner. Two or more types of sensors and/or two or more of the same sensors may be used together to calculate a measurement, and such sensors may be combined or individual. As used herein, the at least one sensor 130 may include individual or combined sensors to measure different or the same data collectively. For example, a three-axis sensor may be a single device that measures parameters and provides data along three axes or may be three single-axis sensor devices or a double-axis sensor device and a single-axis sensor device combined to measure such parameters and provide data along those three axes.

For example, the at least one sensor 130 may include a single axis accelerometer disposed to measure acceleration of a foot in a posterior-anterior direction (i.e., heel to toe, herein referred to as the X direction) and another single axis accelerometer disposed to measure acceleration of a foot in a vertical direction (i.e., heel to knee, herein referred to as the Z direction) or a double axis accelerometer disposed to measure acceleration in the X and Z directions. Or, as another example, the at least one sensor 130 may include a three-axis accelerometer (or any combination of accelerometers measuring fewer axes to total three axes) disposed to measure acceleration of a foot in the X direction, a Z direction, and a lateral direction (i.e., mediolateral, herein referred to as the Y direction). According the exemplary embodiments of the present invention, the at least one sensor 130 may measure only acceleration of the device 100 only in the X and Z directions or may measure only acceleration of the device 100 only in the X, Y, and Z directions to identify various anomalies or occurrences in a walking or running stride. Measuring acceleration of the device 100 along fewer axes and/or measuring only acceleration of the device 100 may decrease cost and weight of the device and allow for broader acceptance and use of the device. For purposes of description, a heel-to-toe direction is herein referred to as a positive (+) X direction, a heel-to-knee direction is referred to as a positive (+) Z direction, and a right direction is referred to as a positive (+) Y direction. Further, the axes as described herein are with reference to a body part, e.g., a foot, such that the axes move when the body part moves.

The memory 140 may store operations and programming of the device 100 accessible and executable by the processor 110 to control the device 100. Further, the memory 140 may store acceleration data measured by the at least one sensor 130, which may include data generated by the at least one sensor 130 and/or information representing data generated by the at least one sensor 130. The memory 140 may also store indicators of anomalies or occurrences within a walking gait or running stride. The memory 140 may be of any type appropriate for storing and allowing access to data and information. The memory 140 may be a non-transitory computer readable storage medium storing instructions that, when executed, cause the processor 110 to perform operations described herein.

The power controller 160 controls power output from the battery 170 and may determine when the device 100 is in use or is not in use. Specifically, if the device 100 is disposed on a shoe of a walker or runner, the power controller 160 may determine whether the device 100 is in use, i.e., whether the walker is walking or the runner is running, and may control output of the battery 170 accordingly. The power controller 160 may control a low power state in which the device 100 is monitored for movement. If movement is detected, the power controller 160 may allow for a change of state of the device from the low power state to an active state for monitoring and measuring movement of the device 100.

The indicator 180 may be disposed to be visible on device 100 when the device 100 is in use while walking or running so as to indicate various states of the device 100 or information from the device 100. For example, the indicator 180 may be a light emitting diode (LED) that turns from green to yellow to red by instruction of the processor 110, for example, as the runner approaches mileage targets that were previously defined and associated with the different color modes of the LED. The LED color mode can be used to provide the runner with progression indications regarding a wear condition of an associated shoe. Further, the indicator 180 may additionally or separately indicate a sate of or information from the device 100 via haptic feedback, for example, via vibration of the device 100.

The device 100 includes a display 190 to provide information while the device 100 is in use while walking or running and/or while the device 100 is not tracking physical activity, i.e., while at rest. The display 190 may provide a readout of a number of miles run on the associated shoes and/or other information associated with the current and/or past activities based on the determinations according to aspects of the present invention. For example, the display 190 may display cadence, average cadence, distance, pace, average pace, footstrike, etc. The display 190 may also display information related to searches and/or recommendations for products based on information and data detected by the at least one sensor 130. Further, the display 190 and the indicator 180 as described herein may be incorporated into one feature or may remain separate as described.

The processor 110 is connected to and communicates with the memory 140 to manage and operate each of the features of the device 100 including each of the communication interface 120, the at least one sensor 130, the memory 140, the I/O interface 150, the power controller 160, the battery 170, the indicator 180, and the display 190. The processor 110 may be an onboard computer processing unit (CPU) that manages the device 100 and each of the features of the device 100. The processor 110 may perform calculations on the raw data provided by the at least one sensor 130 and may record anomalies or occurrences within a walking gait or running stride in the memory 140. The processor 110 may cause the communication interface 120 and/or the I/O interface 150 to transmit raw data and/or information based on the raw data upon or after the occurrence of an anomaly or event. For example, the processor 110 may determine a fall has occurred or may detect a network and transmit data and/or information about the fall to a server or mobile terminal. Further, the processor 110 may incorporate the features of the power controller 160 or such features may remain physically separate.

Figure 2:
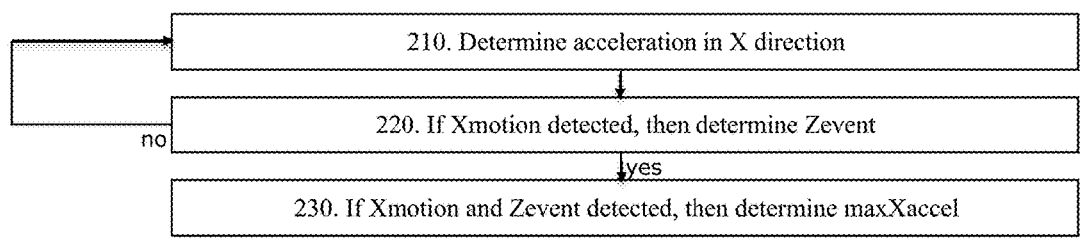
FIG. 2. illustrates a method for determining a footstrike by a device to measure a step of a walker or runner according to aspects of the presently disclosed subject matter.

FIG. 2. illustrates a method for determining a footstrike by a device to measure a step of a walker or runner according to aspects of the presently disclosed subject matter. Specifically, the method illustrated in FIG. 2 accurately measures and determines occurrences of a foot strike on a surface.

According to aspects of the invention, the device described herein is disposed on a body in a manner to capture acceleration of a foot in at least or only the X direction and the Z direction. The X direction and the Z direction may be orthogonal. According to aspects of the invention, the device may additionally capture acceleration of the foot in the Y direction. The Y direction may be orthogonal to at least one of the X direction and the Z direction. Acceleration as used herein is referred to with respect to standard acceleration due to gravity, g, such that 1 g is equal to about 9.81 m/s$^2$ and, for example, 1.39 g is about 13.6 m/s$^2$.

As shown in FIG. 2, the method includes determining a value Xmotion in operation 210, determining a Z event in operation 220, determining a maximum acceleration in the X direction in operation 230.

In operation 210, a value Xmotion, which is an acceleration in the X direction, is determined by the device to indicate the motion of the leg of a walker or runner swinging forward during a step or stride. The value of the acceleration in the X direction, Xmotion, and a time of the value of the acceleration in the X direction, tXmotion, are determined and stored in a memory. The value Xmotion may be determined according to a threshold acceleration, that is, the value Xmotion may be determined when an acceleration in the X direction is greater than a threshold acceleration for at least a specific time. For example, an accelerometer of the device may measure acceleration of the foot in the positive X direction greater than about 1.3 g to 1.5 g for about 70 to 90 ms or more before the device determines that the value Xmotion of the acceleration in the X direction. More particularly, The device may measure the acceleration of the foot in the positive X direction to have a value greater than 1.39 g for 80 ms to determine the value Xmotion and the time tXmotion.

The value Xmotion and the time tXmotion may be determined to be a maximum positive acceleration in the X direction over the 80 ms measured time period and the time tXmotion may be the time corresponding to or at which the maximum positive acceleration in the X direction over the 80 ms is measured. However, aspects need not be limited thereto such that the value Xmotion may be an average acceleration over the time period or may be a discrete default value, for example, the acceleration at the beginning, end, or midpoint of the time period, and the time tXmotion may be determined to correspond to the beginning, midpoint, or end of the time period or be determined to correspond to the time at which the value Xmotion was determined. Further, the time tXmotion may correspond to the value Xmotion but indicate a time separate from a time at which the value Xmotion was measured, e.g., the time tXmotion may indicate the beginning of the measured time period while the value Xmotion was determined in the middle of the measured time period; however, aspects need not be limited thereto. The determined value Xmotion and the determined time tXmotion are stored in the memory and/or output from the device at the control of the processor.

The determination of the value Xmotion and the time tXmotion may open at least one window for evaluation and determination of various other values and times. For example, if the value Xmotion and the time tXmotion are determined, the device may begin evaluating acceleration of the foot for a time in a second direction, e.g., the Z direction. Further, the device may begin evaluating, in the same or another one or more windows, acceleration of the foot for determination of the foot landing or contacting a surface, i.e., a footstrike, and/or for determination of the foot leaving the surface after a footstrike, i.e., a push off.

For example, the determination of the value Xmotion may open a first window in which acceleration in the Z direction is evaluated for the determination of an event in the Z direction, i.e., a Zevent. In operation 220, the device determines whether the measured acceleration in the Z direction meets the criteria for determination of the event Zevent. Here, the determination of the event Zevent in the first window according to aspects of the present disclosure indicates that the foot is being prepared for the footstrike, i.e., being prepared for landing on a surface, and is moving down before impact with the surface. If no event Zevent is determined to occur in the first window, the device returns to operation 210 to measure the acceleration of the foot to determine the value Xmotion.

The event Zevent may be determined when appropriate criteria are determined. For example, the event Zevent may be determined if a first criteria and a second criteria are satisfied. The determination of the criteria may be required within a specific time. The first criteria may be a determination of parameters in the Z direction. The first Zevent criteria may be determined if at least one of a first and second condition are determined to be measured in the first window. Here, the first window may be a window in which the device evaluates acceleration information in the Z direction for a time of 225 to 275 ms, for example, for 250 ms. The first condition of the first criteria for determining the occurrence of the event Zevent in the first window is determining whether the foot has an acceleration in the negative Z direction, i.e., down from knee to heel, has a magnitude greater than a first threshold for a time period. For example, the first condition determines whether the foot has a change in an acceleration in the negative Z direction having a magnitude greater than, for example, a transient threshold over a transient time period. The transient threshold may be, for example, 0.1 to 1.0 g, and the transient time period may be, for example, 5 to 25 ms. For example, the transient threshold may be 0.25 g or 0.5 g, and the transient time period may be 10 ms. The first condition may be referred to as a transient condition in which a change in acceleration is measured over a period of time. For example, as used herein, a transient property, e.g., criteria, condition, determination, etc., may be determined as a change in an acceleration having a magnitude greater than or less than a transient threshold over at least a transient time period. The change in acceleration may be positive, negative, or a magnitude. Here, the first condition with respect to the negative Z direction may be referred to as −Ztrans. As an example, the first condition may be determined by taking a difference between an acceleration in the Z direction at time 0 and time 10 ms. If the difference between the acceleration in the Z direction at time 0 and time 10 ms is greater than the transient threshold, for example, 0.25 g, then the first condition is satisfied. However, aspects are not limited thereto such that determinations of the differences in acceleration, herein and throughout, may be measured instantaneously, i.e., jerk.

The second condition of the first criteria for determining the occurrence of the event Zevent in the first window is whether the foot has an acceleration in the negative Z direction having a magnitude greater than a second threshold. The second threshold may be, for example, 0.75 to 2.0 g, for example, 1.0 g or 1.8 g. The second threshold may be referred to as an event threshold. The second criteria may indicate that the foot in a latter portion of a swing and approaching the ground before impact.

The second criteria for determination of the event Zevent may be determined when an event Xevent occurs after the first criteria for the event Zevent is determined. The event Xevent may be determined to indicate that the foot is no longer swinging or moving forward. The event Xevent condition may be satisfied when the acceleration in the X direction is less than a threshold after the first criteria for determining the event Zevent is satisfied. For example, the threshold for the event Xevent may be an acceleration in the X direction less than 1.5-2.5 g, for example, less than 2 g. However, aspects need not be limited thereto such that the event Xevent may be determined according to acceleration over time or differences in acceleration over time. For example, the event Xevent may be determined if a difference between accelerations in the X direction over 10 to 15 ms is greater than a threshold, for example, 2 to 3 g, for example, 2.5 g. In other words, the event Xevent may be determined as a 10 or 15 ms transient acceleration of 2.5 g. Or, for example, the event Xevent may be determined when acceleration in the X direction is greater than the threshold within a 10 to 15 ms time period. The event Xevent may be determined to occur at any point within the time period, for example, the actual time of occurrence or a default point, for example, the beginning or end of the time period.

If either or both of the first condition and the second condition of the first criteria for determining the occurrence of the event Zevent occur and the second criteria for determining the occurrence of the event Zevent occurs as determined in Operation 210 to have occurred in the first window after the determination of the value Xmotion in Operation 210, then a value max Xaccel and a time max tXaccel of a maximum acceleration in the X direction in the first window is determined in operation 230. Specifically, the value of the maximum acceleration in the X direction after the determination of the value Xmotion and the determination of the event Zevent is determined as the value Footstrike, which indicates the foot has contacted a surface, i.e., a footstrike. Further, the time of maximum acceleration in the X direction after the determination of the value Xmotion and the determination of the event Zevent is determined as the time of the footstrike, i.e., tFootstrike. The value Footstrike and the time tFootstrike are stored in the memory and/or output from the device at the control of the processor. The accurate determination of the value Footstrike and the time tFootstrike make possible the identification of anomalies in less powerful gaits and strides, i.e., in older individuals.

However, aspects need not be limited thereto such that the value Footstrike may be determined according to other criteria. For example, the value Footstrike may be determined as the value max Xaccel within a time period after the event Xevent. For example, the value Footstrike may be determined as the value max Xaccel within a time period after the event Xevent of 100 to 150 ms, for example, 125 ms. The value Footstrike may be determined as the largest acceleration in the negative Z direction within a time period after time at which the value Xmotion is determined to have occurred, for example, 200 to 300 ms, for example, 250 ms after the time at which the value Xmotion is determined to have occurred, i.e., the time tXmotion.

Further, if one or more of the various conditions and criteria are not satisfied, then the device may return to operation 210 for determination of the value Xmotion. For example, the device may return to operation 210 if the first condition of the first criteria is determined to not occur within a time period with reference to the determination of the value Xmotion. For example, the device may return to operation 210 if the first condition of the first criteria is determined to not occur within 120 to 180 ms after the beginning of the period over which the value Xmotion is determined in operation 210.

Figure 3:
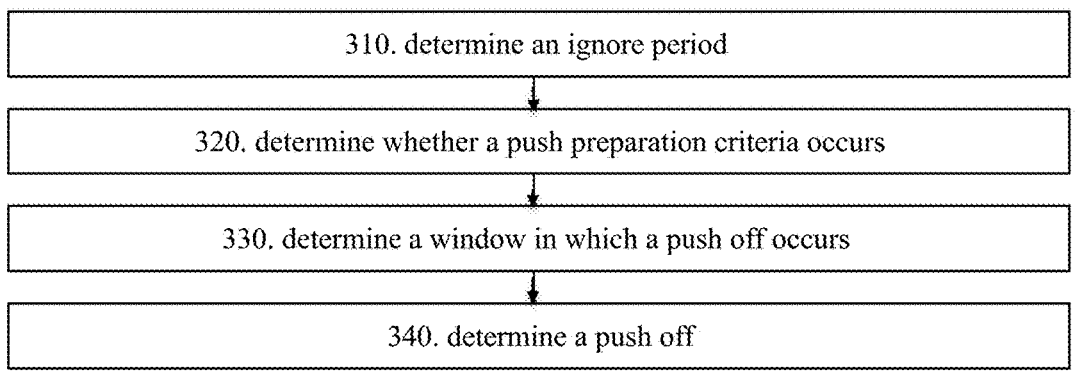
FIG. 3 illustrates a method for determining a push off of a foot from a surface by a device to measure a step of a walker or runner according to aspects of the presently disclosed subject matter.

FIG. 3 illustrates a method for determining a push off of a foot from a surface by a device to measure a step of a walker or runner according to aspects of the presently disclosed subject matter. Specifically, the method illustrated in FIG. 3 measures and determines an occurrence of a foot lifting off the ground, i.e., pushing off the ground, after a footstrike to begin swinging into the next step or stride. The method as illustrated in FIG. 3 includes determining an ignore period in Operation 310, determining whether a push preparation criteria occurs in Operation 320, determining a window in which a push off occurs in Operation 330, and determining a push off in Operation 340.

In Operation 310, an ignore period is determined as the greater of a first ignore period equal to the time tXmotion, as described with respect to FIG. 2, plus an ignore factor, for example, 225 to 275 ms, and a second ignore period equal to the time tFootstrike, as described with respect to FIG. 2, plus an ignore factor, for example, 100 to 150 ms. Further, the ignore period may be set as a default value, for example, 100 to 500 ms. The ignore period may be set as 140 ms after the time at which the value Footstrike is determined to have occurred, i.e., the time tFootstrike. The determined ignore period provides for stabilization of the device and the accelerometers after the footstrike. After the occurrence of the determined ignore period in Operation 310, the acceleration values of the foot as determined by the device are monitored for occurrences of at least one push preparation criteria to determine that the foot is preparing to push off from the surface in Operation 320. For example, the first push preparation criteria is a transient criteria in the X direction and is satisfied when the foot has a change in acceleration in the X direction having a magnitude greater than, for example, a transient threshold, for example, of 0.2 to 0.5 g, for example, 0.25 g or 0.45 g, over a transient time period of 10 ms. The second push preparation criteria is a transient criteria in the Z direction and is satisfied when the foot has a change in acceleration in the Z direction having a magnitude greater than, for example, the transient threshold of 0.25 g over the transient time period of 10 ms. The third push preparation criteria is satisfied when the acceleration in the X direction is determined to be greater than an event threshold for a time period, for example, 1.5-2.5 g for at least 5-15 ms. For example, the third push preparation criteria may be satisfied when the acceleration in the X direction is determined to be greater 2 g for 10 ms. The values of the accelerations and the times of the values of the accelerations that meet the first, second, and third push preparation criteria are determined and stored in the memory or output from the device at the control of the processor.

If at least one of the first, second, and third push preparation criteria is satisfied, a push off window is determined and accelerations of the foot in the X and Z directions are monitored and determined in Operation 330. The push off window is determined to be the shorter of a first push off window and a second push off window. The first push off window is a time measured from the time tXmotion plus a time at which the at least one of the first, second, and third push preparation criteria is satisfied, i.e., tPushPrep, plus 225 ms. In other words, the first push off window is the time period from the time tXmotion to 225 ms after the time tPushPrep. The second push off window is the time tXmotion, as described with FIG. 2, plus 1335 ms. However, aspects need not be limited thereto such that the push off window may be a time period, for example, 200 to 300 ms, after one or more of the push preparation criteria are satisfied. For example, the push off window may be 250 ms after the first push preparation criterion is satisfied.

In Operation 340, the acceleration value PushOff is determined as being the greater of the maximum acceleration in the X direction and the maximum acceleration in the Z direction within the push off window as determined in Operation 330. A time of the value PushOff, i.e., tPushOff, is also determined in Operation 340. The value PushOff and the time tPushOff are stored in the memory and/or output from the device at the control of the processor. If no push off is determined within the push off window, the device returns to operation 210 of FIG. 2 to measure the acceleration of the foot to determine the value Xmotion. However, aspects need not be limited thereto such that the value PushOff may be determined as the maximum acceleration in the X direction. The accurate determination of the value PushIOff and the time tPushOff additionally make possible the identification of anomalies in less powerful gaits and strides, i.e., in older individuals.

Using the determined times tPushOff of multiple steps or strides, a cadence, i.e., a number of footstrikes per minute, of the walker or runner may be determined. Further, because the accuracy of the determination of the footstrike and the push off, accuracy of the cadence is increased. Accuracy of the cadence is also increased by determining the push off of the foot within the push off window because push offs occurring outside of the second push off window may not be included for average cadence and/or standard deviation of the average cadence.

Cadence may be calculated by first determining a stride time, which is tPushOff(n) to tPushOff(n+1). Then, because stride time is generally measured in milliseconds per step, cadence for one foot equals (60000 ms/min)/(stride time ms/step), which results in steps per minute for one foot. To determine the cadence for two feet, the determined one foot cadence is multiplied by 2.

Figure 4:
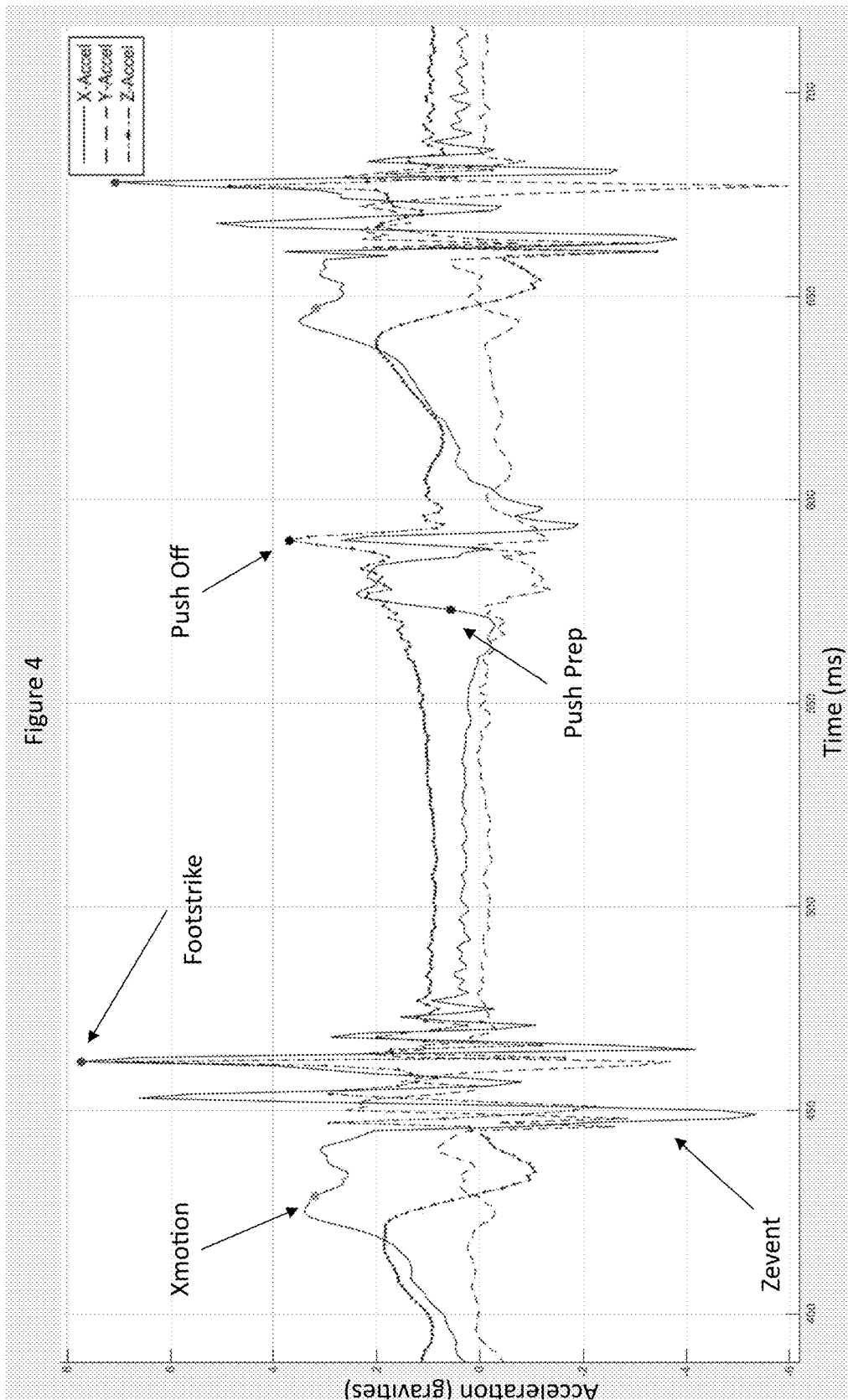
FIG. 4 is a graph illustrating accelerometer information of a device to measure a step of a walker or a runner according to aspects of the presently disclosed subject matter.

FIG. 4 is a graph illustrating accelerometer information of a device to measure a step of a walker or a runner according to aspects of the presently disclosed subject matter. As shown in FIG. 4, the value Xmotion is indicated and is determined as having a magnitude greater than 1.39 g for 80 ms. After the value Xmotion has been determined according to aspects of the present disclosure, the event Zevent is determined as indicated in FIG. 4. In this case, both the first and second criteria for determining the event Zevent are satisfied in that the acceleration in the negative Z direction is greater than 0.25 g for 10 ms and the acceleration in the X direction is less than 2 g. And, as indicated in FIG. 4, after both the value Xmotion and the event Zevent have been determined, the value of the maximum acceleration in the X direction is determined as the value Footstrike, which indicates the foot has contacted a surface, i.e., a footstrike.

Further, after the value Footstrike is determined as indicated in FIG. 4, the first push preparation criteria, as described herein, is determined to be satisfied and Xtrans is indicated also in FIG. 4. After the push preparation criteria are determined to have been satisfied, the value PushOff is determined and shown in FIG. 4.

Figure 5:
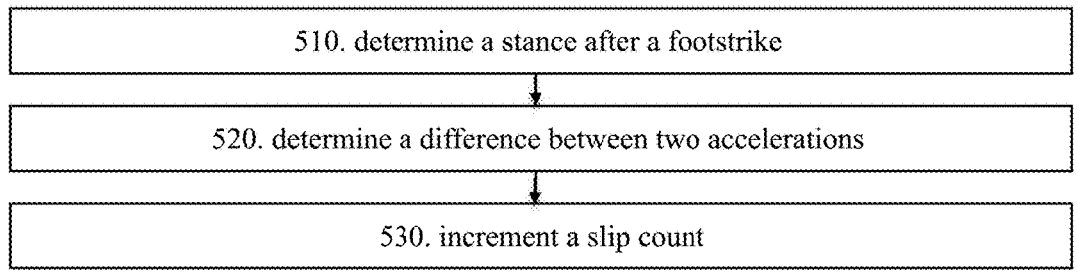
FIG. 5 illustrates a method for determining a slip of a foot by a device to measure a step of a walker or runner according to aspects of the presently disclosed subject matter.

FIG. 5 illustrates a method for determining a slip of a foot by a device to measure a step of a walker or runner according to aspects of the presently disclosed subject matter. A slip of a foot occurs while the foot is on a surface, i.e., after the footstrike as described in FIG. 2 and before the push off of the foot from the surface as described in FIG. 3. As such, the method as described herein with respect to FIG. 5 may be combined with the methods as described herein with respect to FIGS. 2 and/or 3; however, aspects need not be limited thereto such that the method as described herein with respect to FIG. 5 may be combined with other methods of determining a footstrike, determining a push off, and/or other methods described herein.

The method as illustrated in FIG. 5 includes determining a stance after a footstrike in Operation 510, determining a difference between two accelerations in Operation 520, and incrementing a slip count in Operation 530.

In Operation 510, acceleration information of at least the X direction and the Z direction are determined by the device to determine whether stance criteria are satisfied to indicate a stance, i.e., that the foot is disposed on a surface after the footstrike. If at least the measured accelerations of the device in the X direction and in Z direction are within stance ranges for a period of time, then the stance conditions may be determined to be satisfied. For example, if at least the measured acceleration of the device in the X direction is between 0 and 1 g and the measured acceleration of the device in Z direction is between 0 and 1 g for 25 ms, the stance conditions are determined to be satisfied in operation 510. If the stance conditions are satisfied for a continuous 25 ms in Operation 510, then the difference between the acceleration in the Z direction and the X direction is determined in Operation 520. If the acceleration in the Z direction is greater than the acceleration in the X direction by at least a slip threshold, for example, 0.5 to 1.5 g for more than a period of time, for example, 30 to 50 ms, then a slip is determined to occur, and a slip count is incremented to indicate the occurrence of the slip. The slip threshold may be 1 g and the period of time may be 40 ms. The incremented slip count may be stored in the memory and/or output from the device at the control of the processor. Further, if a slip is determined to occur, the method may return to Operation 210 of FIG. 2 to determine acceleration of the foot in the X direction.

However, aspects need not be limited thereto as additional conditions may be included in determining the stance of the foot. For example, according to aspects of the present disclosure, the stance conditions may further include determining the acceleration in the Y direction such that if the measured acceleration in the Y direction is within a stance range for a time period, then the additional stance condition is determined to be satisfied in Operation 510. For example, the stance range in the Y direction may be −0.5 g and 0.5 g, and the time period may be 25 ms. In such case, if the stance conditions for the X, Y, and Z directions are satisfied for a continuous 25 ms in Operation 510, then the difference between the acceleration in the Z direction and the X direction is determined in Operation 520. If the acceleration in the Z direction is greater than the acceleration in the X direction by at least the slip threshold for more than a time period, then a slip is determined to occur, and a slip count is incremented to indicate the occurrence of the slip. The determination of a slip may be output via the display and/or indicator of the device, and/or may be transmitted via text, email, audible alarm, electronic communication or notification, and the like to another device, a mobile terminal, a computer, a server, a user, a healthcare professional, and the like so as to indicate that a slip has occurred.

Figure 6:
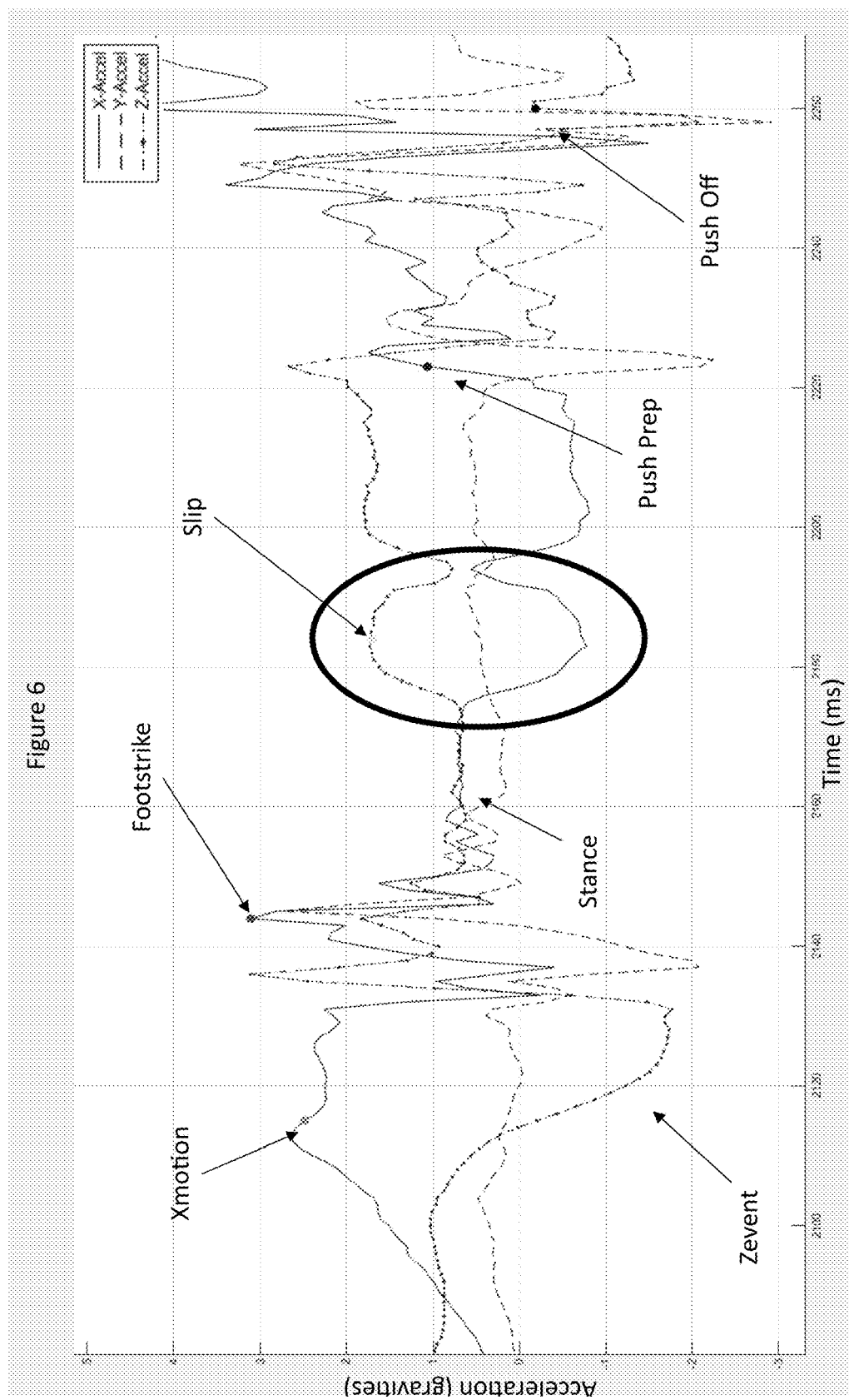
FIG. 6 is a graph illustrating accelerometer information of a slip as determined by a device to measure a step of a walker or runner according to aspects of the presently disclosed subject matter.

FIG. 6 is a graph illustrating accelerometer information of a slip as determined by a device to measure a step of a walker or a runner according to aspects of the presently disclosed subject matter. As shown in FIG. 6, after a footstrike and before a push off, a stance is determined in which at least the measured acceleration of the device in the X direction is between 0 and 1 g and the measured acceleration of the device in Z direction is between 0 and 1 g for 25 ms. Then, a slip is indicated in which the acceleration in the Z direction is greater than the acceleration in the X direction by at least 1 g for more than 40 ms.

Figure 7:
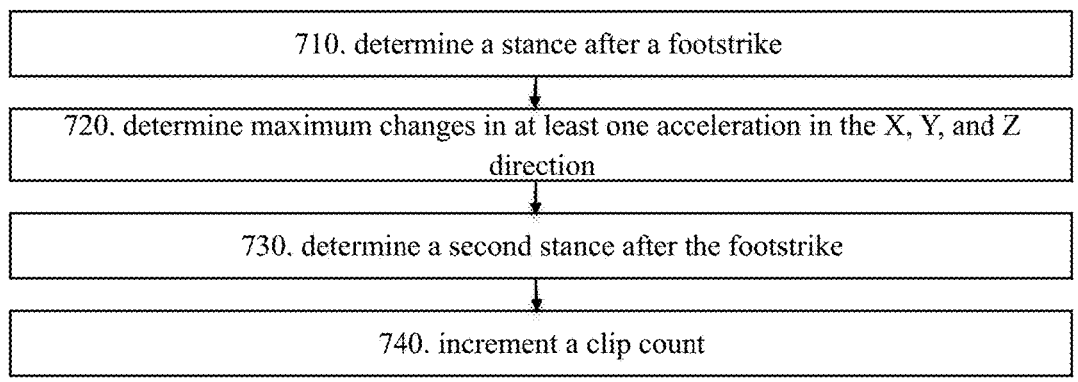
FIG. 7 illustrates a method for determining contact between feet while walking or running by a device to measure a step of a walker or runner according to aspects of the presently disclosed subject matter.

FIG. 7 illustrates a method for determining contact between feet while walking or running by a device to measure a step of a walker or runner according to aspects of the presently disclosed subject matter. Specifically, when feet and legs are in motion while walking or running, the swinging foot, which moves past the stationary foot, i.e., a foot meeting the stance conditions as described herein, may contact, i.e., clip, the stationary foot as the swinging foot moves past the stationary foot. Frequency of the swinging foot clipping the stationary foot may indicate a fatigue or instability of a step, and, thus, be used to predict injury or falling.

The swinging foot clipping the stationary foot occurs while the stationary foot is on a surface, i.e., after the footstrike as described in FIG. 2 and before the push off of the foot from the surface as described in FIG. 3. As such, the method described herein with respect to FIG. 7 may be combined with the methods as described herein with respect to FIGS. 2 and/or 3. Similarly, the method described herein with respect to FIG. 7 may be combined with the methods as described herein with respect to FIGS. 2, 3, and/or 5. However, aspects need not be limited thereto such that the method as described herein with respect to FIG. 7 may be combined with other methods of determining a footstrike, a slip, and/or determining a push off.

The method as illustrated in FIG. 7 includes determining a stance after a footstrike in Operation 710, determining of maximum changes in at least one acceleration in the X, Y, and Z direction in Operation 720, determining a second stance after the footstrike in Operation 730, and incrementing a clip count in Operation 740.

In Operation 710, acceleration information of at least the X direction and the Z direction are determined by the device to determine whether stance criteria are satisfied to indicate a stance, i.e., that the foot is disposed on a surface after the footstrike. If at least the measured accelerations of the device in the X direction and in Z direction are within stance ranges for a period of time, then the stance conditions may be determined to be satisfied. For example, if at least the measured acceleration of the device in the X direction is between 0 and 1 g and the measured acceleration of the device in Z direction is between 0 and 1 g for 30 ms, the stance conditions are determined to be satisfied in operation 710. If the stance conditions are satisfied for a continuous 30 ms in Operation 710, then maximum changes in acceleration in each of the X, Y, and Z directions are determined. The maximum changes in acceleration in each of the X, Y, and Z directions may be determined over 1 ms or more. For example, the maximum changes in acceleration in each of the X, Y, and Z directions may be determined over 2, 3, 5, 8 ms or more. The maximum changes in acceleration may be determined discretely as differences between accelerations at two time points or may be determined instantaneously.

For example, in the X direction, the maximum of the difference between the acceleration information in the X direction at time (t) and the acceleration information in the X direction at time (t−1) and the difference between the acceleration information in the X direction at time (t+1) and the acceleration information in the X direction at time (t) is determined. Similarly, in the Y direction, the maximum of the difference between the acceleration information in the Y direction at time (t) and the acceleration information in the Y direction at time (t−1) and the different between the acceleration information in the Y direction at time (t+1) and the acceleration information in the Y direction at time (t) is determined. And, in the Z direction, the maximum of the difference between the acceleration information in the Z direction at time (t) and the acceleration information in the Z direction at time (t−1) and the different between the acceleration information in the Z direction at time (t+1) and the acceleration information in the Z direction at time (t) is determined. If the absolute values of each of the maximum differences in acceleration in each of the X, Y, and Z directions are greater than a clip threshold in Operation 720, then a second stance is determined in Operation 730. The clip threshold may be, for example, 0.3 to 0.4 g/ms, and may be about 0.35 g/ms.

However, aspects need not be limited thereto such that a clip may be determined in Operation 720 if an acceleration greater than a clip threshold in each of the X, Y, and Z directions are determined to occur within a specific time period; for example, if an impulse greater than a clip threshold of 0.35 g/ms in each of the X, Y, and Z directions are determined to occur within 5 ms of each other, a clip may be determined.

In Operation 730, a second stance is determined. Here, the second stance may be similar to the stance determined in Operation 710. For example, if at least the measured acceleration of the device in the X direction is between 0 and 1 g and the measured acceleration of the device in Z direction is between 0 and 1 g for 30 ms, the second stance conditions are determined to be satisfied in operation 730. If the second stance conditions are determined to be satisfied in operation 730, then a clip is determined to occur, and a clip count is incremented in Operation 740 to indicate the occurrence of the clip. The incremented clip count may be stored in the memory and/or output from the device at the control of the processor.

Figure 8:
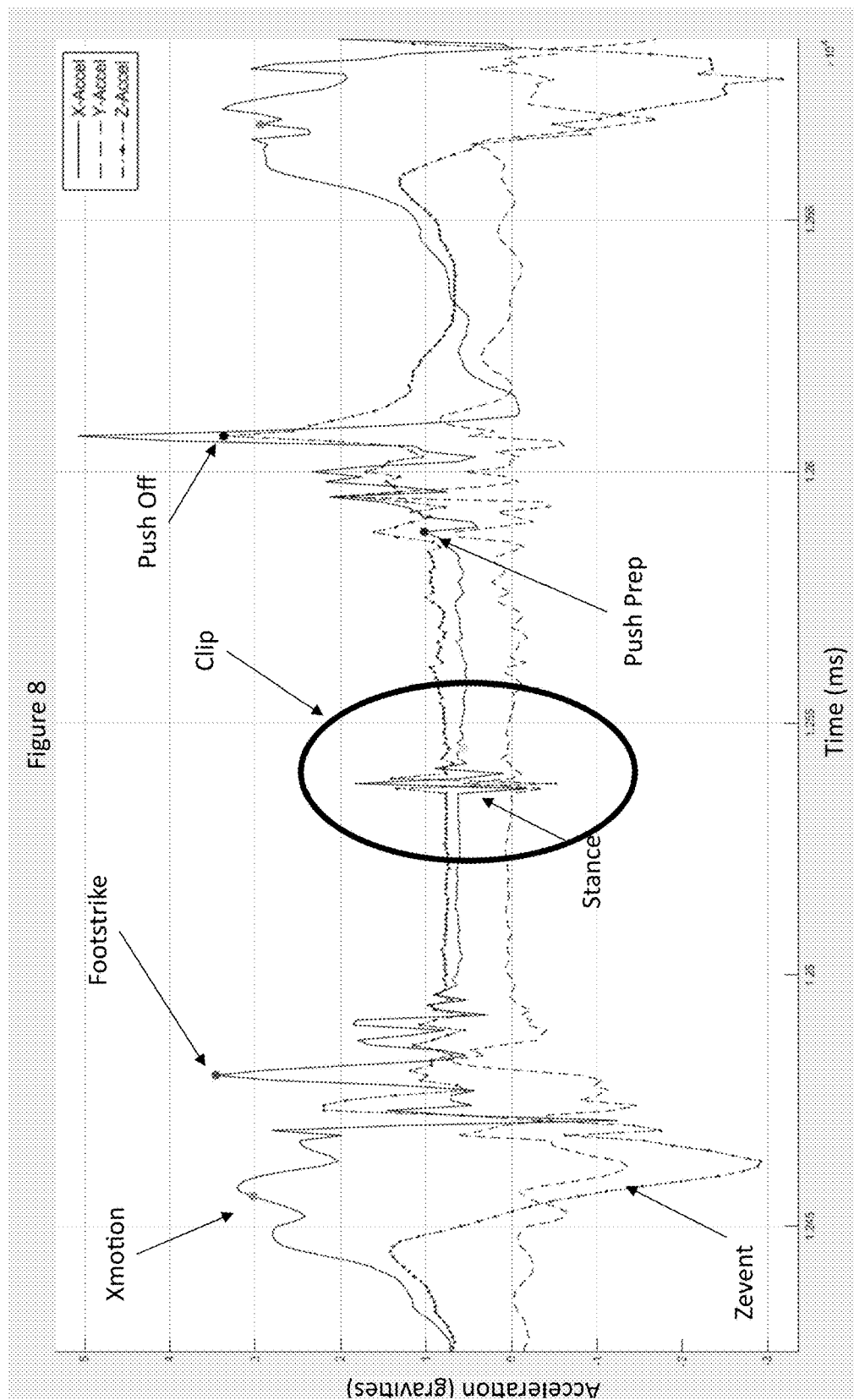
FIG. 8 is a graph illustrating accelerometer information of a clip as determined by a device to measure a step of a walker or runner according to aspects of the presently disclosed subject matter.

However, aspects need not be limited thereto as additional conditions may be included in determining the stance in Operation 710 and the second stance in Operation 740. For example, according to aspects of the present disclosure, the stance conditions may further include determining the acceleration in the Y direction such that if the measured acceleration in the Y direction is between −0.5 g and 0.5 g for 30 ms, the additional stance condition is determined to be satisfied in Operations 710 and 740. Further, the second stance as determined in Operation 740 may be limited to a maximum period for determination, for example, 35 to 50 ms, for example 45 ms, after the maximum absolute values of the differences in the X, Y, and Z directions such that if the second stance is determined to exceed 45 ms, then the method may return to Operation 210 of FIG. 2 to determine acceleration of the foot in the X direction. The determination of a clip may be output via the display and/or indicator of the device, and/or may be transmitted via text, email, audible alarm, electronic communication or notification, and the like to another device, a mobile terminal, a computer, a server, a user, a healthcare professional, and the like so as to indicate that a clip has occurred FIG. 8 is a graph illustrating accelerometer information of a device to measure a step of a walker or a runner according to aspects of the presently disclosed subject matter. As shown in FIG. 6, after a footstrike and before a push off, a stance is determined in which at least the measured acceleration of the device in the X direction is between 0 and 1 g and the measured acceleration of the device in Z direction is between 0 and 1 g for 30 ms. Then, a clip is indicated in which the maximum changes in acceleration in each of the X, Y, and Z directions are each determined to be greater than, for example, 0.35 g. And, a second stance is determined in which at least the measured acceleration of the device in the X direction is between 0 and 1 g and the measured acceleration of the device in Z direction is between 0 and 1 g for at least 30 ms. Further, in each of the stances, stance conditions may further be determined according to acceleration in the Y direction being between −0.5 g and 0.5 g as shown in FIG. 8.

Figure 9:
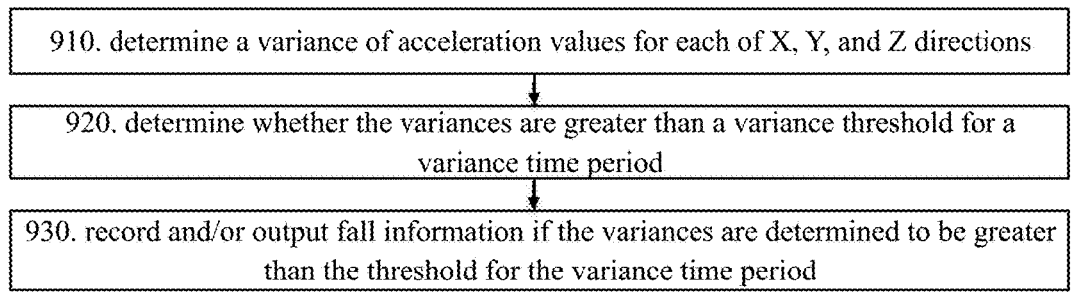
FIG. 9 illustrates a method for determining a fall by a walker or a runner by a device to measure a step of a walker or runner according to aspects of the presently disclosed subject matter.

FIG. 9 illustrates a method for determining a fall by a walker or a runner by a device to measure a step of a walker or runner according to aspects of the presently disclosed subject matter. The acceleration profiles that indicate that a walker or runner has fallen are different from those that indicate a footstrike, a push off, a slip, or a clip, and require different analysis. A fall may be indicated when the measured accelerations in each of the X, Y, and Z directions vary greatly over a time period. For example, the variations of the accelerations in one or more of the X, Y, and Z directions may be determined according to variance, standard deviation, root mean squared error, change within a moving window average or coefficient of variation.

The method of FIG. 9 includes determining a variation of the acceleration values for each of the X, Y, and Z directions in operation 910, determining whether the variation is greater than a variation threshold for a variation time period in Operation 920, and recording and/or outputting fall information if the variation is determined to be greater than the threshold for the variation time period in Operation 930.

In Operation 910, variations for accelerations in each of the X, Y, and Z directions are determined. The determined variations may be variances and may be determined according to Equation 1:

$$\mathrm{Var} = \frac{\left[\sum (Accel \times Accel)\right] - \left[\frac{\left[\sum Accel \times \sum Accel\right]}{n}\right]}{n-1}.$$

Equation 1

In Equation 1, Var is the determined variance for a direction, Accel is the acceleration value for the direction, and n is the duration of the data evaluated. According to aspects of the present disclosure, n may be 50 to 150 ms, for example, 125 ms.

After the variations are determined in Operation 910, each of the determined variations is compared to a variation threshold. The variation threshold may be the same for each of the X, Y, and Z directions or the variation threshold may be different for one or more of the X, Y, and Z directions. For example, in Operation 920, if the determined variation is a variance of the acceleration in the X direction for the duration n and is greater than 6, the determined variation is a variance of the acceleration in the Y direction for the duration n and is greater than 4, and the determined variation is a variance of the acceleration in the Z direction for the duration n and is greater than 6 for greater than or equal to the variance time period, then a fall may be determined to have occurred. The variation time period may be 40 to 60 ms, for example, 50 ms, or longer. If one of the determined variations of the acceleration in the X, Y, and Z directions decreases to less than the respective variation threshold within the variation time period, then the variation determinations are reset and determined again.

If a fall is determined to have occurred in Operation 920, the fall may be stored in memory and/or output from the device at the control of the processor in Operation 930. For example, upon the determination of the occurrence of the fall, an alarm from the device may be output audibly and/or visibly. Further, the device may transmit an alarm or cause an alarm to be transmitted via text message, email, pop-up, telephone call, electronic communication or notification, or any other alert method, to indicate that a fall has been determined to occur.

Further, falls may occur at any time during a step such that the method described herein with respect to FIG. 9 may be combined with the methods as described herein with respect to FIGS. 2 and/or 3. Similarly, the method described herein with respect to FIG. 9 may be combined with the methods as described herein with respect to FIGS. 2, 3, 5, and/or 7. However, aspects need not be limited thereto such that the method as described herein with respect to FIG. 9 may be combined with other methods of determining a footstrike, a slip, clip, and/or determining a push off.

Figure 10:
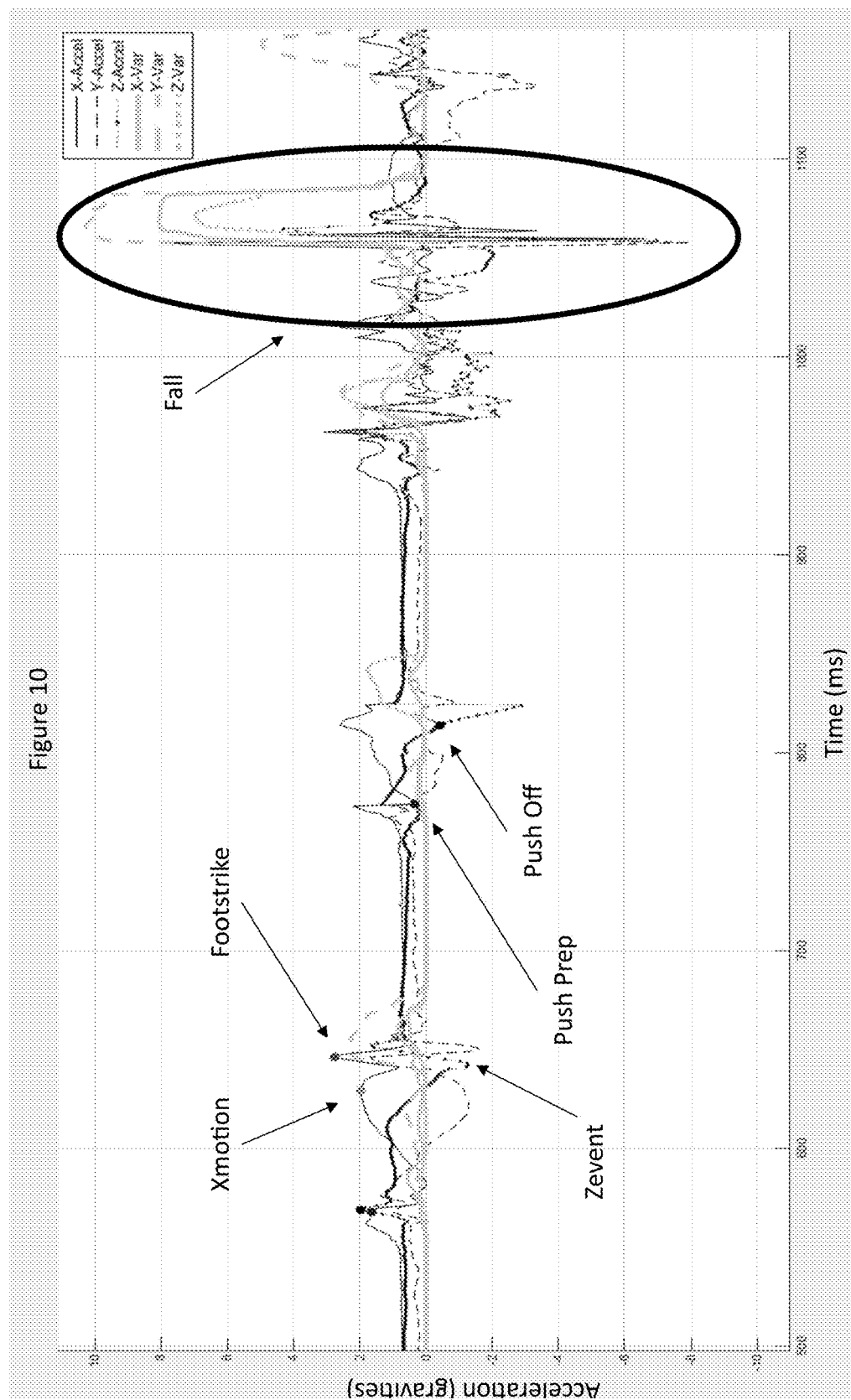
FIG. 10 is a graph illustrating acceleration variation information of a fall as determined by a device to measure a step of a walker or a runner according to aspects of the presently disclosed subject matter.

FIG. 10 is a graph illustrating accelerometer information of a device to measure a step of a walker or a runner according to aspects of the presently disclosed subject matter. As shown in FIG. 10, the variations of each of the accelerations of the foot in the X, Y, and Z directions are greater than the respective variation thresholds for each of the X, Y, and Z directions to thereby indicate that a fall has occurred.

Figure 11:
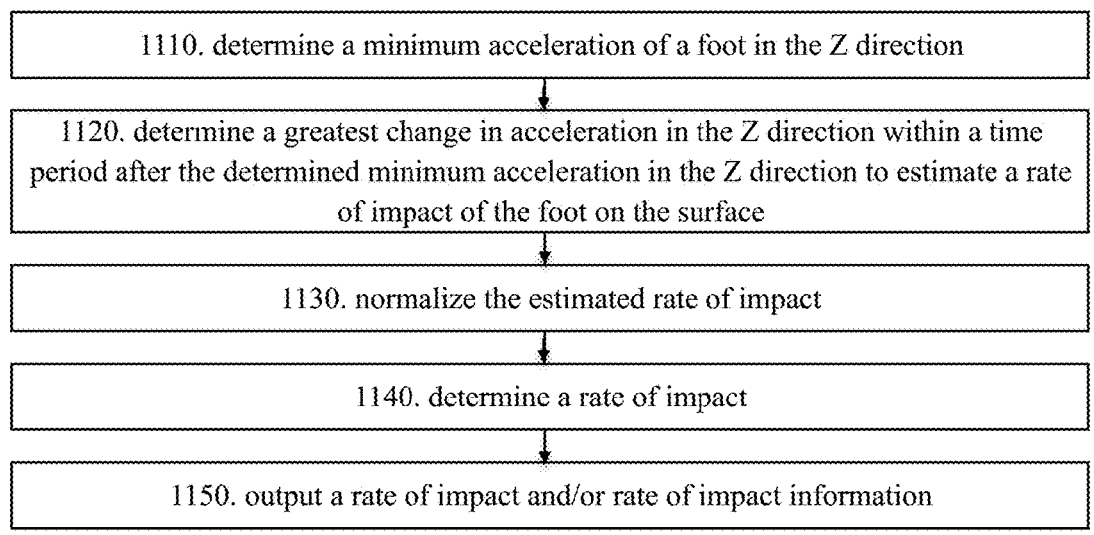
FIG. 11 illustrates a method for determining an injury risk by a walker or a runner by a device to measure a step of a walker or runner according to aspects of the presently disclosed subject matter.

FIG. 11 illustrates a method for determining an injury risk by a walker or a runner by a device to measure a step of a walker or runner according to aspects of the presently disclosed subject matter.

Rate of impact is a measure of a rate in which a walker or runner loads their leg upon impact of their foot on the surface, i.e., rate of impact is a measure of the rate in which a walker or runner loads their leg upon footstrike. And, the rate of impact is indicative of tibial stress fracture risk. According to aspects of the present disclosure, the rate of impact may be determined to be within about 20 to 80% of a change in the acceleration of the foot in the Z direction upon or near footstrike.

The method illustrated in FIG. 11 includes determining a minimum acceleration of a foot in the Z direction in Operation 1110, determining a greatest change in acceleration in the Z direction within a time period after the determined minimum acceleration in the Z direction to estimate a rate of impact of the foot on the surface in Operation 1120, normalizing the estimated rate of impact in Operation 1130, determining a rate of impact in Operation 1140, and outputting a rate of impact and/or rate of impact information in Operation 1150.

In Operation 1110, a minimum acceleration of the device in the Z direction, minZ, is determined after the value of the acceleration in the X direction, Xmotion, is determined in Operation 210 of FIG. 2. The minimum acceleration of the device in the Z direction minZ is the acceleration in the negative Z direction having the greatest magnitude after the value Xmotion is determined as described herein.

In Operation 1120, a greatest amount of change in acceleration is determined as an estimated rate of impact eROI in an impact time period after the minimum acceleration of the device in the Z direction minZ. For example, the impact time period may be 15 to 25 ms after the determined minimum acceleration in the Z direction minZ. The impact time period may be, for example, 20 ms after the determined minimum acceleration in the Z direction minZ.

In Operation 1130, the estimated rate of impact eROI is normalized by first determining greatest accelerations in the X direction maxX and the Z direction maxZ after the determined minimum acceleration in the Z direction minZ. If the maximum acceleration in the Z direction maxZ divided by 8 is less than 0.7, the estimated rate of impact eROI is normalized to the maximum acceleration in the Z direction maxZ. For example, if the maximum acceleration in the Z direction maxZ divided by 8 is less than 0.7, then the normalized rate of impact normROI is equal to the estimated rate of impact eROI multiplied by the maximum acceleration in the Z direction maxZ divided by 8, i.e., ROInorm=eROI*MaxZ/8. If the maximum acceleration in the Z direction maxZ divided by 8 is greater than or equal to 0.7, the estimated rate of impact eROI is normalized to the maximum acceleration in the X direction maxX. For example, if the maximum acceleration in the Z direction maxZ divided by 8 is greater than or equal to 0.7, then the normalized rate of impact normROI is equal to the estimated rate of impact eROI multiplied by the maximum acceleration in the X direction maxX divided by 8, i.e., ROInorm=eROI*MaxX/8.

In Operation 1140, a rate of impact ROI is determined from the normalized rate of impact ROInorm. For example, the rate of impact ROI, in bodyweights BW per second, may be determined to be equal to 18.5+(7.5*ROInorm). However, aspects need not be limited thereto such that the rate of impact may be determined by various other equations and determinations.

In Operation 1150, the determined rate of impact ROI and/or rate of impaction ROI information is stored in the memory and/or output from the device according to control of the processor. For example, if the determined rate of impact ROI is determined according to Operation 1140 to be less than 64 BW/s, then the rate of impact ROI information may be set to "No Risk" and may be indicated by an indicator and/or a display of the device. If the determined rate of impact ROI is determined according to Operation 1140 to be greater than or equal to 64 BW/s and less than or equal to 80 BW/s, then the rate of impact ROI information may be set to "Moderate Risk" and may be indicated by an indicator and/or a display of the device. If the determined rate of impact ROI is determined according to Operation 1140 to be greater than 80 BW/s, then the rate of impact ROI information may be set to "High Risk" and may be indicated by an indicator and/or a display of the device. Further, if the determined rate of impact ROI is determined according to Operation 1140 to be greater than 150 BW/s, then an error may be returned and may be indicated by an indicator and/or a display of the device. The rate of impact ROI information may indicate a risk of tibial stress fracture or other walking and/or running related injury. The determination of the rate of impact ROI may be output via the display and/or indicator of the device, and/or may be transmitted via text, email, audible alarm, electronic communication, and the like to another device, a mobile terminal, a computer, a server, a user, a healthcare professional, and the like.

Further, consideration of other factors may be taken into account when predicting a likelihood of injury from walking or running and may be included in the rate of impact ROI information. For example, other factors for consideration may be increased mileage of walking or running, shoe rotation, cadence variability, stance variability, shoe replacement, increased stance time, and the magnitude of the force of impact of the foot without regard for bodyweight.

Although describe herein with respect to walking and running, aspects of the present invention need not be limited thereto such that the teachings and disclosures herein may be applied to other activities, for example, snow skiing and snow boarding, water skiing and wakeboarding, cycling, skateboarding, fitness classes and exercises, roller skating, and the like. Some alterations may be necessary, however, for analysis of different activities; for example, in analysis of skateboarding, Y direction determinations may need to be substituted for X direction determinations as described herein, and vice versa.

Further, aspects of the present invention may be modified, customizable, or learning in view of input or determined body weight, age, health status, stride length, running or walking style, running or walking conditions, footstrike preference, cadence, equipment, and the like, to provide an increased information and feedback.

Without limitation, the methods as described herein may be implementable in at least one of the device, via controller 900, the terminal, and the server. The exemplary embodiments according to the present invention may be recorded in non-transitory computer-readable media including program instructions to implement various operations embodied by a computer. The media may also include, alone or in combination with the program instructions, data files, data structures, and the like. The media and program instructions may be those specially designed and constructed for the purposes of the present invention, or they may be of the kind well-known and available to those having skill in the computer software arts. Examples of non-transitory computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level is code that may be executed by the computer using an interpreter. The described hardware devices may be configured to act as one or more software modules in order to perform the operations of the above-described embodiments of the present invention.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

We claim:

1. A device to determine characteristics of a step, the device comprising:
    at least one sensor to measure acceleration of a foot in at least two directions;
    at least one processor to execute instructions stored in a memory and to control acceleration data measured by the at least one sensor to be stored in the memory,
    wherein, if the processor determines that acceleration in a first direction is greater than a first direction threshold for a time longer than a first threshold time, and, if the processor determines that acceleration in a second direction meets at least one condition for determination of an event associated with the second direction, the processor determines that the foot impacts a surface;
    wherein, after the foot impacts the surface, the processor determines that the foot slips if a difference between an acceleration in a direction perpendicular to the first direction and an acceleration in the first direction is greater than a slip threshold for at least a slip threshold time after a first stance is determined;
    wherein, after the foot impacts the surface, the processor determines that a swinging foot clips the foot if each of absolute values of each of the maximum differences in acceleration in each of the first direction, a third direction, perpendicular to the first direction, and a fourth direction, perpendicular to the first direction and the third direction, is greater than a clip threshold after a first stance is determined and before a second stance is determined; and
    wherein, if the processor determines that each of variations of accelerations in the first direction, the third direction, perpendicular to the first direction, and the fourth direction, perpendicular to the first direction and the third direction, are greater than a variations threshold for at least a duration, the processor determines that a fall has occurred.

2. The device of claim 1, wherein the processor determines that the foot impacts the surface at a point when the acceleration in the first direction is at a maximum within a time period after the processor determined that the acceleration in the first direction was greater than the first direction threshold for a time longer than the first threshold time.

3. The device of claim 1, wherein the at least one condition for determination of an event associated with the second direction comprises at least one of:
    a change in an acceleration in the negative second direction having a magnitude greater than a transient threshold over a transient time period, and
    an acceleration in the negative second direction having a magnitude greater than an event threshold, the event threshold being greater than the transient threshold.

4. The device of claim 1, wherein, if the processor determines that acceleration in the second direction does not meet the at least one condition for determination of an event associated with the second direction, the processor again determines whether the acceleration in the first direction is greater than the first direction threshold for a time longer than the first threshold time.

5. The device of claim 1, wherein the processor determines a time at which the acceleration in the first direction was greater than the first direction threshold for a time longer than the first threshold time and a time at which the foot impacts the surface, and wherein the processor then implements an ignore phase in which the processor does not analyze data from the at least one sensor for the greater of the time at which the acceleration in the first direction was greater than the first direction threshold for a time longer than the first threshold time plus 250 ms and the time at which the foot impacts the surface plus 125 ms.

6. The device of claim 1, wherein the processor determines a rate of impact of the foot on the surface based on a greatest amount of change in the second direction within a time period after a maximum acceleration in the negative second direction.

7. The device of claim 5, wherein, after the ignore phase, the processor determines a push off of the foot from the surface as the larger of a maximum acceleration in the first direction and a maximum acceleration in the second direction.

8. The device of claim 6, wherein the processor further determines a maximum acceleration in the first direction and a maximum acceleration in the second direction after the maximum acceleration in the negative second direction, and the processor normalizes the greatest amount of change in the second direction within the time period based on at least one of the determined maximum acceleration in the first direction and the determined maximum acceleration in the second direction.

9. A device to determine characteristics of a step, the device comprising:

at least one sensor to measure acceleration of a foot in at least two directions;

at least one processor to execute instructions stored in a memory and to control acceleration data measured by the at least one sensor to be stored in the memory;

the processor determines that a foot has impacted a surface using the acceleration data, thereafter completing a foot stance prior to a following step; and wherein, following the foot stance, if the processor determines that a difference between an acceleration in a second direction perpendicular to the first direction and an acceleration in the first direction is greater than a slip threshold for at least a slip threshold time after the foot stance is determined, the foot is determined to have slipped;

wherein, following the foot stance, if the processor determines that each of absolute values of each of the maximum differences in acceleration in each of the first direction, a second direction, perpendicular to the first direction, and a third direction, perpendicular to the first direction and the second direction, is greater than a clip threshold before a new foot stance is determined, then the foot is determined to have clipped; and wherein, following the foot stance, if the processor determines that each of variations of accelerations in the first direction, the third direction, and the second direction, perpendicular to the first direction and the third direction, are greater than a variations threshold for at least a predetermined duration, a fall is determined to have occurred.

\* \* \* \* \*